(12) United States Patent
Romanick

(10) Patent No.: US 9,208,296 B1
(45) Date of Patent: Dec. 8, 2015

(54) PREVENTION OF USE OF A CONTAMINATED MEDICAL PRODUCT

(71) Applicant: Norman Romanick, Seattle, WA (US)

(72) Inventor: Norman Romanick, Seattle, WA (US)

(*) Notice: Subject to any disclaimer, the term of this patent is extended or adjusted under 35 U.S.C. 154(b) by 0 days.

(21) Appl. No.: 14/724,642

(22) Filed: May 28, 2015

Related U.S. Application Data

(60) Provisional application No. 61/998,101, filed on Jun. 19, 2014.

(51) Int. Cl.
| | |
|---|---|
| *G05B 19/00* | (2006.01) |
| *G05B 23/00* | (2006.01) |
| *A61L 2/00* | (2006.01) |
| *A61N 5/00* | (2006.01) |
| *G06F 21/30* | (2013.01) |
| *A61M 1/36* | (2006.01) |
| *A61L 2/10* | (2006.01) |
| *A61L 2/28* | (2006.01) |

(52) U.S. Cl.
CPC . *G06F 21/30* (2013.01); *A61L 2/10* (2013.01); *A61L 2/28* (2013.01); *A61M 1/36* (2013.01); *A61M 2205/11* (2013.01); *A61M 2205/273* (2013.01); *A61M 2205/276* (2013.01); *A61M 2205/3317* (2013.01)

(58) Field of Classification Search
CPC ......... A61L 2/10; A61L 2202/24; A61L 2/18; A61L 2/28; A61L 2/0011; A61M 2039/167; A61M 25/0017; A61M 1/3681
USPC ................... 340/5.2, 5.1; 422/1, 119, 24, 28; 250/492.1, 455.11
See application file for complete search history.

(56) References Cited

U.S. PATENT DOCUMENTS

| | | |
|---|---|---|
| 1,683,877 A | 9/1928 | Edblom et al. |
| 2,308,516 A | 1/1943 | Knott |
| 2,309,124 A | 1/1943 | Knott |
| 4,737,140 A | 4/1988 | Lee et al. |
| 5,150,705 A | 9/1992 | Stinson |
| 5,702,432 A | 12/1997 | Chen et al. |
| 5,984,887 A | 11/1999 | McLaughlin et al. |
| 8,343,420 B2 | 1/2013 | Cioanta et al. |
| 8,808,977 B2 | 8/2014 | Wu et al. |
| 2004/0039325 A1 | 2/2004 | Karp |
| 2004/0143208 A1 | 7/2004 | Gara |
| 2007/0269876 A1 | 11/2007 | Cordemans de Meulenaer et al. |

(Continued)

OTHER PUBLICATIONS

"Extracorporeal Photopheresis", Stanford School of Medicine, retreived on May 27, 2015 from <<http://cutaneouslymphoma.stanford.edu/community/photopheresis.html>>, 3 pages.

(Continued)

*Primary Examiner* — Mirza Alam
(74) *Attorney, Agent, or Firm* — Lee & Hayes, PLLC

(57) ABSTRACT

This disclosure relates generally to contaminable medical products. In particular, this disclosure provides systems, apparatuses, and methods for preventing contaminated use of medical products that become contaminated upon being used for an intended purpose that requires the operation of a medical treatment apparatus, medical treatment system, or both. A medical product may have a unique identity and a permissive operation session, that is associated with the unique identity, may be created to allow a use of the medical device when uncontaminated, while preventing the use of the medical product after it has been presumably contaminated during the permissive operation session.

18 Claims, 5 Drawing Sheets

(56) References Cited

U.S. PATENT DOCUMENTS

| | | | |
|---|---|---|---|
| 2008/0265179 A1* | 10/2008 | Havens | A61L 2/10 250/492.1 |
| 2009/0212234 A1* | 8/2009 | Vestal | A61L 2/10 250/455.11 |
| 2013/0115132 A1* | 5/2013 | Engimann | A61B 19/02 422/28 |
| 2013/0323117 A1* | 12/2013 | Ma | A61M 39/16 422/1 |
| 2013/0323120 A1* | 12/2013 | Ma | A61L 2/24 422/24 |
| 2014/0030238 A1 | 1/2014 | Perritt et al. | |
| 2015/0165185 A1* | 6/2015 | Cohen | A61L 9/18 128/207.14 |

OTHER PUBLICATIONS

Bailey, "Blogspot—Breathing for a Living", retreived from <<http://leahbailey.blogspot.com/2011/05/photopheresis-z.html>>, May 11, 2011, 4 pages.

"Therapeutic Apheresis Services—Patient Information Leaflet—Extra Corporeal Photopheresis (ECP)", NHS Blood and Transplant, Jul. 2014, 4 pages.

Webpage for Therakos Inc., Retrieved on May 27, 2015 from <<http://www.therakos.co.uk/nurses-or-device-operators/treatment-photopheresis/about>>, 2 pages.

* cited by examiner

PREVENTION OF USE OF A CONTAMINATED MEDICAL PRODUCT

CROSS-REFERENCE TO RELATED APPLICATIONS

The present application claims the benefit of U.S. Provisional Patent Application No. 61/998,101 filed Jun. 19, 2014, which is incorporated herein by reference in their entirety as if fully set forth herein.

FIELD OF THE DISCLOSURE

This disclosure relates generally to contaminable medical products. In particular, this disclosure provides systems, apparatuses, and methods for preventing contaminated use of medical products that become contaminated upon being used for an intended purpose that requires the operation of a medical treatment apparatus, medical treatment system, or both. A medical product may have a unique identity and a permissive operation session, that is associated with the unique identity, may be created to allow a use of the medical device when uncontaminated, while preventing the use of the medical product after it has been presumably contaminated during the permissive operation session.

BACKGROUND

A wide variety of medical products used by the health care industry become contaminated when properly used for an intended purpose. Some of these medical devices are disposable in that they are typically used only a single time before being discarded. For example, extracorporeal blood circuits become contaminated upon use and are typically immediately discarded, as opposed to refurbished for subsequent use, due to the high risk that diseases may spread due to unnecessary exposure to the blood of a patient. Alternatively, some of these medical devices may be refurbished, for example, by being cleaned and sanitized, to extend their useful life such that they may be used multiple times and with multiple patients prior to being discarded. For example, endotracheal tubes are widely refurbished and reused by anesthesiologists living in developing countries. Refurbishing an endotracheal tube includes cleaning the endotracheal tube with soap and water, scrubbing it with a brush to remove all blood and mucus, and finally sterilizing it by, for example, soaking it in CIDEX® OPA Solution. Reusing a contaminated medical product, either on the same patient or a subsequent patient, can spread disease and is a major concern within the health care industry.

BRIEF DESCRIPTION OF THE DRAWINGS

The detailed description is described with reference to the accompanying figures. The same reference numbers in different figures indicate similar or identical items.

DETAILED DESCRIPTION

Figure 1:
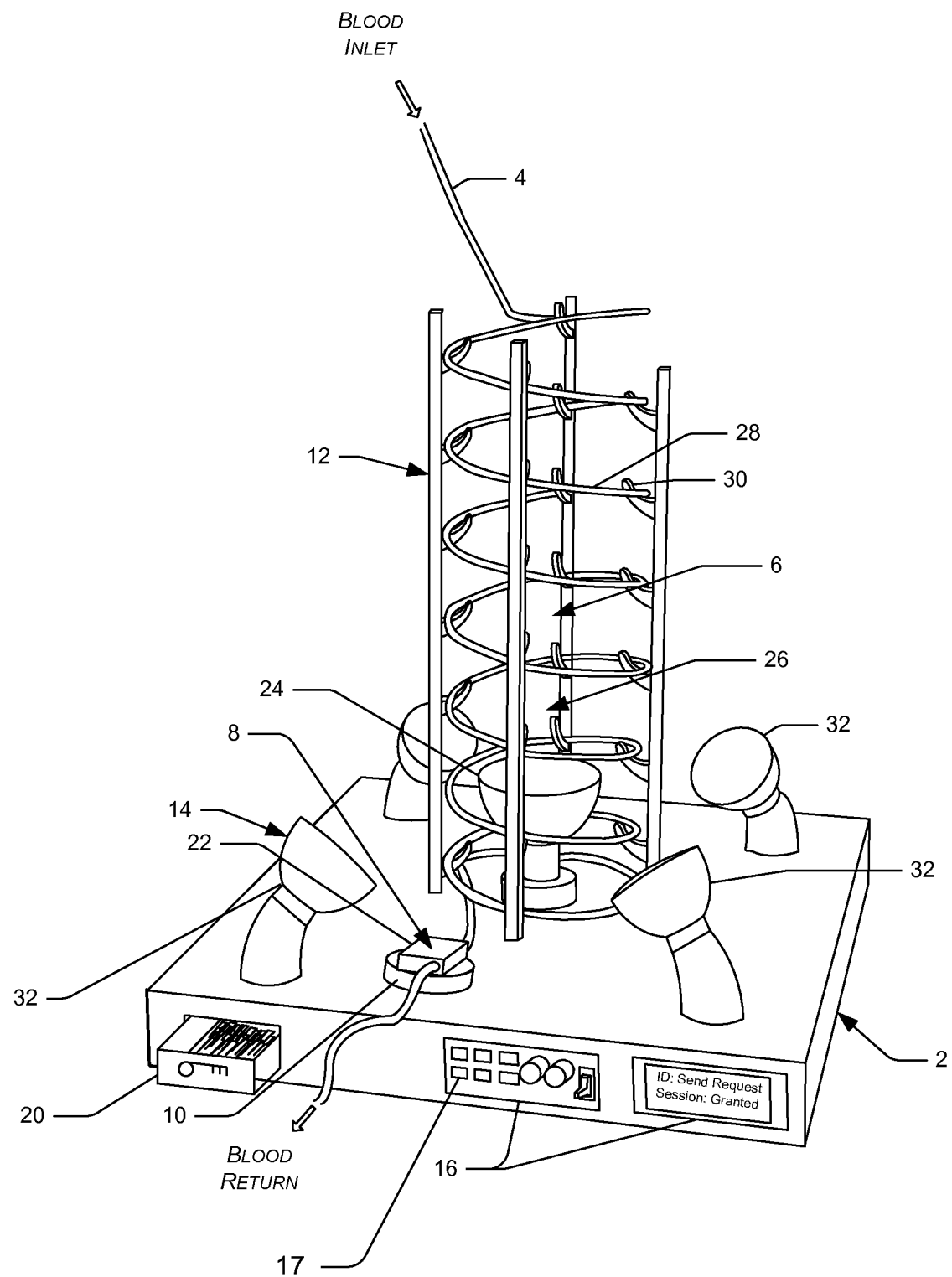
FIG. 1 illustrates a medical treatment apparatus supporting an extracorporeal blood circuit (EBC) within an exposure region for controlled exposure of blood to electromagnetic (EM) radiation during a treatment session, wherein the EBC includes an identification tag and the medical treatment apparatus includes a tag reader, in accordance with a first embodiment of the present disclosure.

This disclosure provides systems, apparatuses, and methods for preventing contaminated use of a medical product that becomes contaminated upon being used for an intended purpose that requires the operation of a medical treatment apparatus. It is an object of the present disclosure to prevent unnecessary spread of disease, bacteria, or any other contaminants, during a medical treatment session by preventing the operation of the medical treatment apparatus, and thus the use of the medical product for its intended purpose, unless the medical device is determined to be in an acceptable condition for use. Upon receiving a request to use the medical treatment apparatus, a determination of a usage status of the medical device may be made by looking up a unique identity associated with the medical device in a usage log and, responsive to the determination, the request may be granted if the usage status is below a usage status threshold, or may be denied if the usage status is above a usage status threshold.

In various embodiments, a medical device for the treatment of blood in an extracorporeal blood circuit (EBC) includes an EBC that has an identification tag defining a unique identity associated with the EBC, a support element for maintaining the EBC within an exposure region, and one or more exposure devices for exposing blood circulating through the EBC to an exposure therapy. For example, a patient's blood circulating through the EBC may be controllably exposed to EM radiation of a specific wavelength and intensity in order to kill blood borne pathogens prior to returning the blood to a patient. In some embodiments, the EBC is configured as a closed circuit in that blood enters the EBC through a blood inlet (FIG. 1), that may be coupled with a needle that is inserted into the patient, and blood exits the EBC through a blood return that may be similarly coupled to a needle. In some embodiments, the medical device may include a controller that is programmed to prevent the exposure device from operating outside of a permissive operation session based on a usage status of the EBC as indicated in a usage log. For example, the controller may determine the unique identity associated with the EBC and then determine, directly or indirectly, the usage status to create a permissive operation session only if the EBC has not been previously used.

In some embodiments, a contaminable medical device that may be refurbished for uncontaminated reuse includes an identification tag to enable usage status logging to prevent use while the medical device is contaminated, e.g., presumably contaminated due to a previous permissive operation session having been created. For example, the contaminable medical device may require the use of a medical treatment apparatus such as, for example, a surgical suction apparatus for removal of surgical fluids, loose tissues, gases, or bodily fluids during a surgical procedure. A controller may prevent the medical treatment apparatus from operating, e.g., providing the suction that is required to use the surgical suction apparatus, following a previous permissive operation session for the surgical suction apparatus, during which the surgical suction apparatus was presumably contaminated. In some embodiments, the previous permissive operation session may have been created in response to a request to use the medical device in conjunction with the medical treatment apparatus and a determination that the medical device has not been previously used, or has been refurbished since a previous use thereof, based on an examination of a usage log. Following the previous permissive operation session, the controller may prevent the medical treatment apparatus from operating for a period of time until the medical device is refurbished for uncontaminated reuse and/or the usage log is updated to indicate the same.

In some embodiments, a system includes a usage logger that is configured to communicate with a medical treatment apparatus via a communication link. A user of the medical treatment apparatus may cause the medical treatment apparatus to send a request, to the usage logger, to create a permissive operation session during which the particular medical product may be used in conjunction with the medical treatment apparatus. The request may include a unique identity associated with the particular medical product for the usage logger to look up in a usage log for determining a usage status, e.g. whether the medical product is "Unused," "Used," or "Refurbished." Upon determining that the usage status is "Unused," or "Refurbished" if the medical product is capable of refurbishment, a response may be transmitted that grants the request by creating a permissive operation session. Upon determining that the usage status is "Used" (e.g. presumably contaminated), a response may be transmitted that denies the request, e.g., does not create a permissive operation session. In some embodiments, the medical treatment apparatus may include a controller to prevent the medical treatment apparatus from operating outside of a permissive operation session.

FIG. 1 illustrates a medical treatment apparatus 2 supporting an extracorporeal blood circuit (EBC) 4 within an exposure region 6 for controlled exposure of blood to EM radiation during a treatment session, wherein the EBC 4 includes an identification (ID) tag 8 and the medical treatment apparatus 2 includes a tag reader 10. In some embodiments, the medical treatment apparatus 2 further includes a support element 12 configured to maintain the EBC 4 in the exposure region 6 during a treatment session such as, for example, exposure of blood within the EBC 4 to controlled EM radiation in the form of ultraviolet (UV) light. Accordingly, some embodiments include one or more exposure devices 14 which may be optionally directed toward the exposure region 6 to expose blood circulating through the EBC during a treatment session to one or more types of exposure therapy, e.g. UV light therapy. In some embodiments, the medical treatment apparatus 2 may include a controller 16 that is programed to prevent the medical treatment apparatus 2 from operating outside of a permissive operation session.

In some embodiments, the controller 16 may be configured to prevent various aspects of the medical treatment apparatus 2 from operating outside of a permissive operation session based on a usage status of the EBC. For example, the controller 16 may be configured to determine the usage status by looking up a unique identity of the EBC 4 in a usage log that stores information related to a plurality of medical products (e.g. a plurality of EBCs and endotracheal tubes and surgical suction tips) including unique identities individually associated with each medical product as well as a usage status of each medical product. For example, two completely fungible medical products may each have a unique identity different than the other (e.g., A001 & A002). During a permissive operation session, the controller 16 may enable all or some aspects of the medical treatment apparatus 2 such as, for example, the one or more exposure device(s) 14 or a blood pump 18 (shown in FIG. 2 further discussed herein) to operate as intended. In contrast, outside of a permissive operation session the controller 16 may disable all, or only some, aspects of the medical treatment apparatus 2. For example, the controller 16 may prevent the blood pump 18 from forcing blood through the EBC 4, or prevent the one or more exposure device(s) 14 operating, or both. Furthermore, because the EBC 4 may potentially be coupled to transfusion needles and attached to a patient prior to the operation of the medical treatment apparatus 2, some embodiments include additional preventative procedure-layers such as, for example, a lock-out drawer 20 which the controller 16 locks-out, e.g., prevents access thereto, outside of a permissive operation session. The lock-out drawer 20 may store essential items for beginning a treatment session, e.g., transfusion needles, so that medical staff cannot commence treatment session preparation and setup prior to a determination being made that the usage status of the medical product is acceptable, e.g. "Unused" or "Refurbished" if applicable.

Figure 3:
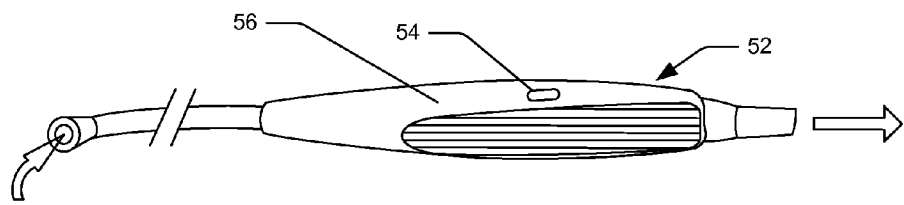
FIG. 3 illustrates a contaminable medical device that requires operation of a medical treatment apparatus for proper use, in accordance with a third embodiment of the present disclosure. The illustrated contaminable medical device requires refurbishment between uses and includes an identification tag, embedded within a handle, to enable usage status logging to prevent the operation of the medical treatment apparatus while the medical device is contaminated.

In some embodiments, the optional tag reader 10 is configured to be read the ID tag 8 of the EBC 4 (or other product in accordance with other embodiments, e.g. as illustrated in FIG. 3 further discussed herein) and communicate information regarding the unique identity associated with the EBC 4 to the controller 16. The ID tag 8 may include a visual graphic such as an alphanumeric identifier or a Quick Response Code (QR code) or a barcode. For example, a medical staffer may obtain a medical product, e.g. the EBC 4, and scan a QR code, embodied on the ID tag 8, with the tag reader 10 which may optionally be a handheld device such as a mobile phone, tablet PC, or a corded QR code scanner coupled to the medical treatment apparatus 2. In various embodiments, the medical staffer may optionally enter an alphanumeric identifier into the medical treatment apparatus 2 manually, e.g. via a keypad 17, without the use of the tag reader 10. In various embodiments, the ID tag 8 may be an EM radiation emitting tag such as, for example, a radio-frequency identification (RFID) tag. Such an RFID tag may be passive or active meaning it may be energized and activated by waves from an outside source or it may include a power source. In some embodiments, the EBC 4 includes an RFID tag embedded within a molded portion 22 of the EBC 4 such that the ID tag is sealed away from any environmental surroundings of the EBC 4. Such an embodiment may enable the medical device to be refurbished for a subsequent use via cleaning and sterilizing the medical device; although it should be appreciated that EBCs are typically used only a single time and immediately discarded.

In some embodiments, the tag reader 10 is fixed in location relative to the support element 12 so that the ID tag 8 is within a range of the tag reader 10 when the EBC 4 is properly installed on the support element and out of range when the EBC is not properly installed. For example, in some embodiments the EBC may be specifically configured to have a correct position when installed on the support element to maximize and/or optimize the effectiveness of the exposure. Accordingly, in some embodiments, the controller 16 may prevent the operation of the various features of the medical treatment apparatus 2 unless the EBC 4 is properly installed or unless the ID tag 8 remains in close proximity to the tag reader 10. The tag reader 10 or ID tag 8, or both, may optionally include one or more magnets to removably secure the ID tag 8 in place during a treatment session. In the event that the ID tag 8 is removed from being adjacent to the tag reader 10, the controller 16 may be configured to sound an alarm (or otherwise alert a patient or medical staffer) and/or halt the operation of one or more various features of the medical treatment apparatus 2.

In some embodiments, the one or more exposure devices 14 include a UV light source 24 disposed within an inner region 26 of a helical shape that the EBC 4 is maintained in by the support element 12. In some embodiments, at least a portion of the EBC 4 is a transparent flexible tube 28 that is maintained in the helical shape by a plurality of hooks 30 (only one of which is labeled). It should be appreciated that the helical shape of the EBC 4 need not be helical to the degree of mathematical precision; rather a generally helical shape is within the scope of the present disclosure. In various embodiments, the one or more exposure devices 14 further include one or more UV light sources 32 (labeled four times) disposed outside of the EBC 4, when maintained in the helical shape by the support element 12. In various embodiments, the one or more exposure devices 14 may be configured to provide exposure to the entire spectrum of EM radiation or any portion thereof. For example, in various embodiments, the one or more exposure devices 14 may provide exposure to infrared EM radiation to blood within the EBC 4. Furthermore, in some embodiments, the transparent flexible tube 28 has a profile configured with a predetermined surface area to volume ratio to optimize an intensity of exposure to blood flowing through the transparent flexible tube 28. For example, in an embodiment wherein the transparent flexible tube 28 has a circular profile, as the diameter of the profile is increased so does the exposure intensity to the blood flowing through the transparent flexible tube 28.

Figure 2:
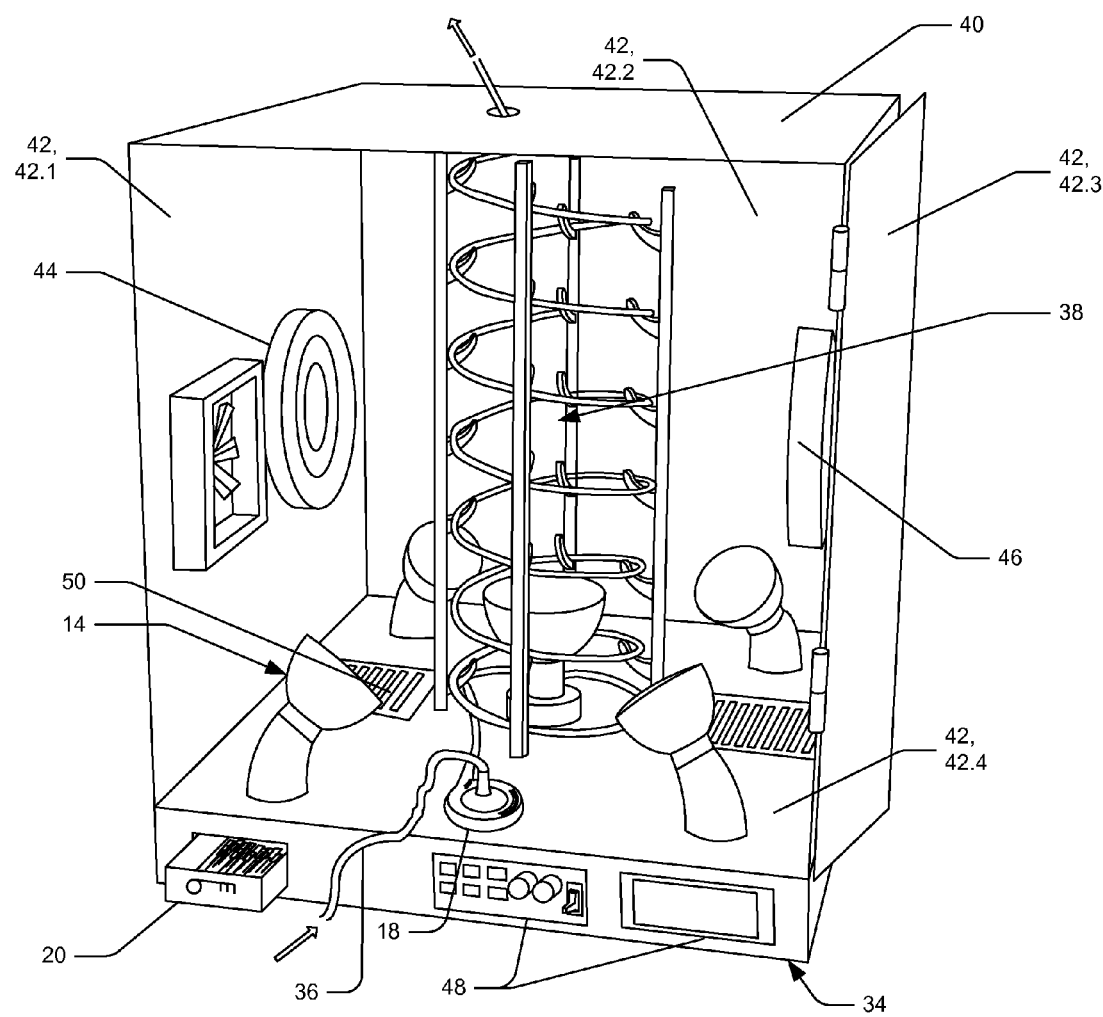
FIG. 2 illustrates a medical treatment apparatus supporting an EBC within an exposure region for controlled exposure of blood to EM radiation within a housing that includes a reflective internal surface to redirect ultraviolet light toward the extracorporeal blood circuit, in accordance with a second embodiment of the present disclosure. The illustrated medical treatment apparatus of FIG. 2 further includes an electromechanical speaker(s) for controlled exposure of blood to acoustic pressure waves.

FIG. 2 illustrates a medical treatment apparatus 34 supporting an extracorporeal blood circuit (EBC) 36 within an exposure region 38 for controlled exposure of blood to electromagnetic radiation within a housing 40 that includes a reflective internal surface(s) 42 to redirect ultraviolet light toward the EBC 36. The illustrated medical treatment apparatus 34 further includes one or more electromechanical speakers 44 for controlled exposure of blood to acoustic pressure waves.

In some embodiments, the reflective internal surface(s) 42 (labeled four times) is a mirrored surface such that it is configured to perform specular reflection, e.g. light rays from a single incoming direction are reflected into a single outgoing direction. In some embodiments, the reflective internal surface(s) 42 is configured to perform diffuse reflection, e.g. light rays incoming from a single direction are reflected in multiple outgoing directions. For example, the reflective internal surface(s) 42 may be designed to resemble, as closely as practicable based on engineering and design constraints, the reflective properties of a white body that reflects all incident rays completely and uniformly in all directions. In various embodiments, the reflective internal surface(s) 42 is configured to absorb one or more wavelengths of electromagnetic (EM) radiation. For example, the internal reflective surface(s) 42 may be configured to absorb substantially all incident EM radiation such as by designing the internal reflective surface with an emissivity as close to 1.0 as practicable. It should be appreciated that the internal reflective surface(s) 42 may include one or more discretely identifiable sub-surfaces (42.1, 42.2, 42.3, 42.4) and that it is within the scope of this disclosure that any of the surface properties herein may be practiced in combination such as, for example, by having different sub-surfaces exhibit different properties, or by having different portions of a single sub-surface exhibit different properties, or both.

In some embodiments, the medical treatment apparatus 34 includes one or more electromechanical speakers 44 for controlled exposure of blood to acoustic pressure waves. For example, the electromechanical speakers 44 may be configured to expose blood flowing through the EBC 36 to sound of varying frequencies, or intensities, or both. In some embodiments, the electromechanical speakers 44 produce ultrasound waves. For example, ultrasound waves may be directed toward the blood to produce varying degrees of cavitation to neutralize one or more types of bacteria. In various embodiments, the electromechanical speakers 44 may be configured to direct infrasonic sound waves toward the exposure region 38.

In some embodiments, the medical treatment apparatus 34 includes an electromagnetic field (EMF) generator 46 to controllably raise a level of magnetic flux density within the exposure region 38. For example, the EMF generator 46 may be controlled by a controller 48 to selectively increase the Guass exposure to blood within the EBC 36. In some embodiments, the EMF generator 46 is configured to raise the Guass exposure to above 12 milliGuass (mG).

In some embodiments, the medical treatment apparatus 34 includes a blood pump 18 to perfuse blood through the EBC 36 during a treatment session. The pump 18 may be in communication with the controller 48 and the controller 48 may be programmed to prevent the blood pump 18 from operating outside of a permissive use session. For example, a single use disposable blood pump may require a power source to be supplied from the medical apparatus 34 in order to operate. The controller 48 may withhold the power source from the pump 18 outside of a permissive use session as determined by a usage status of the EBC 36. In various embodiments, the pump 18 may be integrated with the EBC 36, e.g. the EBC 36 may be attached to the pump 18 and packaged in a sanitary state to be opened immediately prior to a treatment. The ID tag 8 may optionally be integrated into a plastic molded portion of the blood pump 18. It should be appreciated that, as with other features of the present disclosure, the blood pump 18 is optional equipment. Accordingly, in some embodiments, a blood pump is not used at all but rather blood is perfused through the EBC 36 via pressure from the patient's circulatory system and/or gravity.

In some embodiments, the medical treatment apparatus 34 includes one or more heat units 50 to controllably raise the temperature within the exposure region 38. For example, one or more electric-resistance heating elements may be configured to output a predefined wattage or range of wattages based on an input from the controller 48. In various embodiments, the one or more heat units 50 may include a heat pump unit configured to reduce the temperature within the exposure region 38. For example, a condenser may be configured to remove heat from within the housing 40 thereby reducing the temperature to which blood within the EBC 36 is exposed.

In some embodiments, the medical treatment apparatus 34 is configured to be used for one or more acceptable purposes despite being outside of a permissive use session associated with a particular uniquely identifiable medical product. For example, the controller 48 may be configured to enable a medical staffer to use the one or more exposure devices 14 for the acceptable purpose of sterilizing surgical instruments even outside of a permissive use session. In doing so, the medical staffer may indicate to the controller 48, via a keypad entry for example that that one or more contaminated medical instruments have been placed within the exposure region and are ready for sterilization. The controller 48 may then enable the operation of the UV lights or the heat unit, or both, to sterilize the medical instruments, e.g. a scalpel.

FIG. 3 illustrates a contaminable medical device 52 that requires operation of a medical treatment apparatus, e.g. a surgical suction pump, for proper use. The illustrated contaminable medical device 52 may require refurbishment between uses and may include an ID tag 54, embedded within a handle, to enable usage status logging to prevent the operation of the medical treatment apparatus while the medical device 52 is contaminated. Refurbishment may include one or both of cleansing various debris from the contaminable medical device 52, or sterilizing the contaminable medical device 52, or both. In some embodiments, an indication may be provided to a usage logger, as discussed below, that the contaminable medical device 52 has been refurbished and is in an acceptable condition for a subsequent use. In some implementations, the indication of refurbishment may only be provided by an entity or a system that performs the refurbishment so as to avoid false indications of refurbishment. For example, refurbishment of the contaminable medical device 52 may require being put through a washing cycle of a sanitizing system, e.g. many contaminable surgical devices are reused after having been sanitized in a system resembling of an industrial dishwashing system. In some implementations, such a refurbishment system may be configured to alter a usage status associated with the contaminable medical device 52 only after the device 52 has been both checked into the sanitizing system at the beginning of a wash cycle and checked out of the sanitizing system at the end of the wash cycle. Furthermore, in various embodiments, the ID tag 54 is embedded within the contaminable medical device 52 to protect the ID tag 54 from damage or interference during use or cleaning. For example, the device 52 may be a surgical suction device (as illustrated) for removing blood, or other contaminable substance, from an area during a surgery. The device 52 may include a handle 56 made of plastic or stainless steel, for example, and the ID tag 54 may be embedded within the handle 56 so that the ID tag 54 is completely protected from exposure to contaminants during the surgery, water and chemicals during the washing, cycle, and any other environmental elements. Accordingly, the device 52 may be used and cleaned without risk of damaging or otherwise interfering with the ID tag 54. Although the disclosure discloses features of the contaminable medical device 52 with relation to a surgical suction device, this example is not intended to be limiting and it should be appreciated that other contaminable devices are also contemplated.

Figure 4:
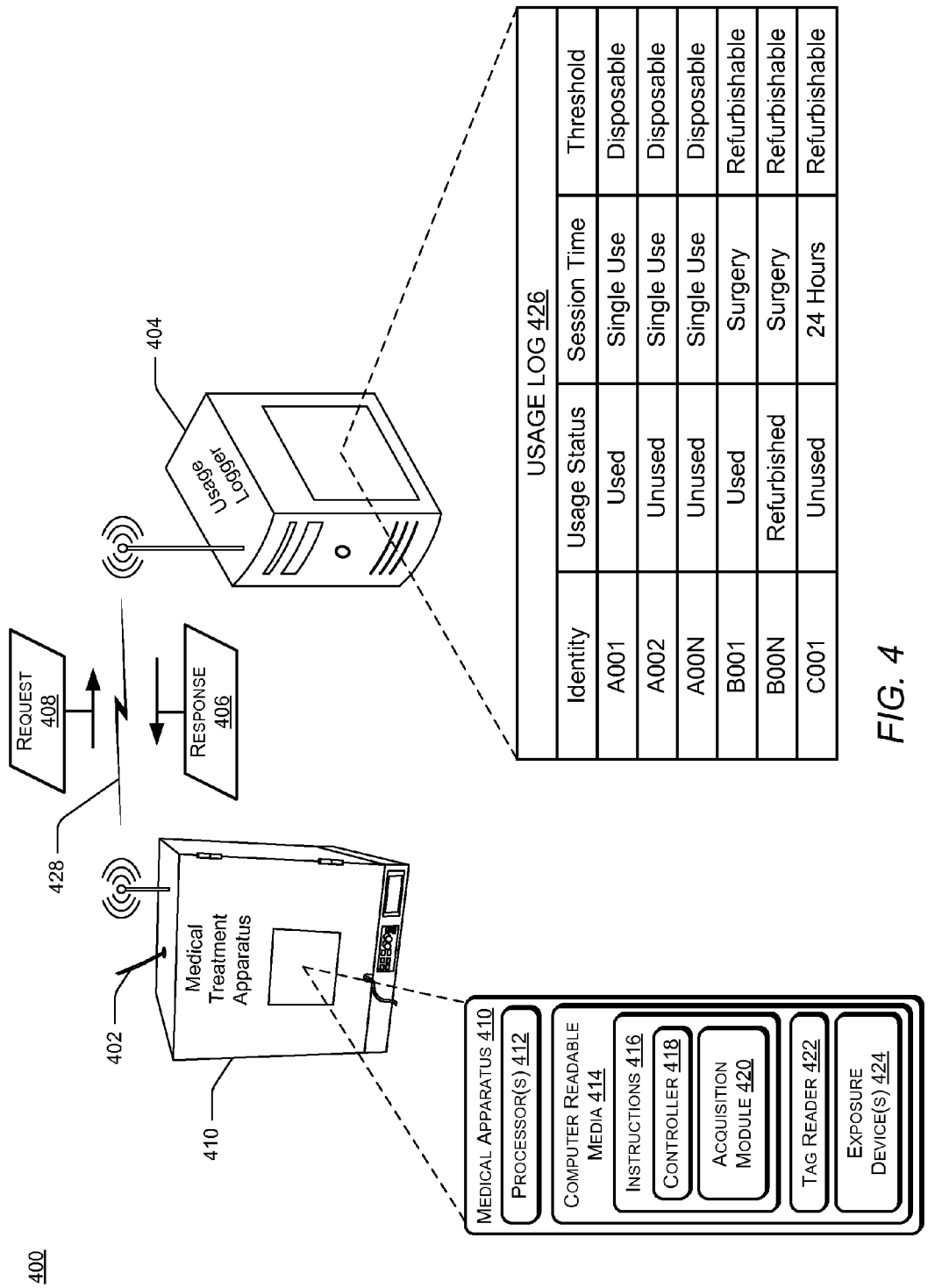
FIG. 4 is a diagram of an exemplary system for preventing contaminated use of a medical product. The system includes a usage logger to log a usage status associated with a unique identity of the medical product and to respond to requests to use a medical treatment apparatus in conjunction with the medical product.

FIG. 4 is a diagram of an exemplary system 400 for preventing contaminated use of a medical product 402 (shown as an EBC but other medical devices may replace the EBC within the scope of this disclosure). The system includes a usage logger 404 to log a usage status associated with a unique identity of the medical product 402 and to transmit a response 406 to a request 408 to use a medical treatment apparatus 410.

In some embodiments, the medical treatment apparatus 410 may include one or more processor(s) 412 and/or one or more computer readable media 414. The computer readable media 414 may include volatile storage (e.g., random-access memory) and/or non-volatile memory (e.g., a hard disk or another type of non-volatile memory). The computer readable media 414 may be used to store software instructions 416, such as device drivers, an operating system, and/or software applications that are executable by the processors 412 to perform various functions. In some embodiments, the instructions 416 may also include information and/or restrictions with regard to specific types of treatment, including but not limited to exposure times and intensities, associated with particular medical conditions to prevent a treatment type that may be incompatible or harmful or ineffective with regard to a particular patient.

The computer readable media 414 may further include a controller module 418 to control various components of the medical treatment apparatus 410. For example, the controller 418 may be configured to prevent one or more exposure devices 424 from operating outside of a permissive use session and/or prevent a lock-out drawer 20 from opening until a unique identity of a medical product has been entered that has an acceptable usage status, e.g. unused or refurbished, and a permissive operation session corresponding to the unique identity has been created. It should be appreciated that controller 418 may be similar to controller 16 from FIG. 1 and/or controller 48 from FIG. 2.

In some embodiments, the medical apparatus 410 further includes a usage status acquisition module 420 configured to send a request 408 to the usage logger 404 to obtain a usage status as indicated in a usage log 426.

In some embodiments, the medical apparatus 410 may establish a communication (COM) link 428 with the usage logger 404 to send and/or receive information, e.g. a request 408 or a response 406. In some embodiments, the COM link 428 is established through one or more Wireless Local Area Networks (WLANs) such as, for example, a private Wi-Fi network which the medical apparatus 410 is configured to connect. In some embodiments, the COM link 428 is established through one or more long-range networks such as a cellular network and/or a satellite based connection to enable the COM link 428 to be maintained even when the medical apparatus is outside of the range of a LAN or WLAN.

In some implementations, the usage logger 404 includes a server that maintains the usage log 426 and updates the usage log 426 based on, for example, the transmission of a response which creates permissive operation sessions or the reception of an indication that a medical device has been refurbished. For example, a medical product with identity B00N is shown in the usage log 426 as having been refurbished subsequent to its most recent use, i.e. the usage status is "Refurbished". Accordingly, upon receiving a request to create a permissive operation session of the medical treatment apparatus 410 to enable the use of medical product B00N, a response may be transmitted which grants the request by creating a permissive operation session to allow use of B00N. However, upon receiving a request to create a permissive operation session of medical product A001 or B001, a response may include a denial of the request. In an alternative embodiment, the usage logger 404 may not send a response at all if the usage status is not such that a permissive operation session should be created.

In some embodiments, the medical treatment apparatus 410 includes a tag reader 422 to read an ID tag on a medical product. For example, in an embodiment wherein the medical apparatus 410 is a surgical vacuum to provide suction to a surgical suction tip such as depicted in FIG. 3, a surgeon may scan the ID tag 54 (FIG. 3) using the tag reader 422 to provide a unique identity of the surgical suction tip, e.g. B00N, to the controller 418 which transmits a request 408 to the usage logger 404. The usage logger 404 may then determine that the usage status of B00N is "Refurbished" and the Session Time of an applicable permissive operation session is "Surgery" meaning a single surgical procedure. The usage logger 404 may then transmit a response 406 to the medical treatment apparatus 410 which creates a permissive operation session which lasts for a single surgical procedure.

In some implementations, the usage status acquisition module 420 is further configured to send the usage logger 404 a usage status update, e.g. via the COM link 428, that indicates that a particular uniquely identified medical product has presumably been used, e.g. a permissive operation session was created for the particular uniquely identified medical product. The usage logger 404 may then update the usage log 426 based on the usage status update. For example, if the medical device B001 (which is indicated as "Used" in the usage log 426) has been refurbished since its last use then a usage status update may cause the usage logger to update the usage status of B001 to "Refurbished" thereby enabling a subsequent permissive use session to be created. As another example, if medical device A001 is a type of device for which refurbishment is not acceptable, for example the "Session Time" is equal to "Single Use," the usage logger 426 may take no action in response to a usage status update indicating that A001 has been refurbished.

Figure 5:
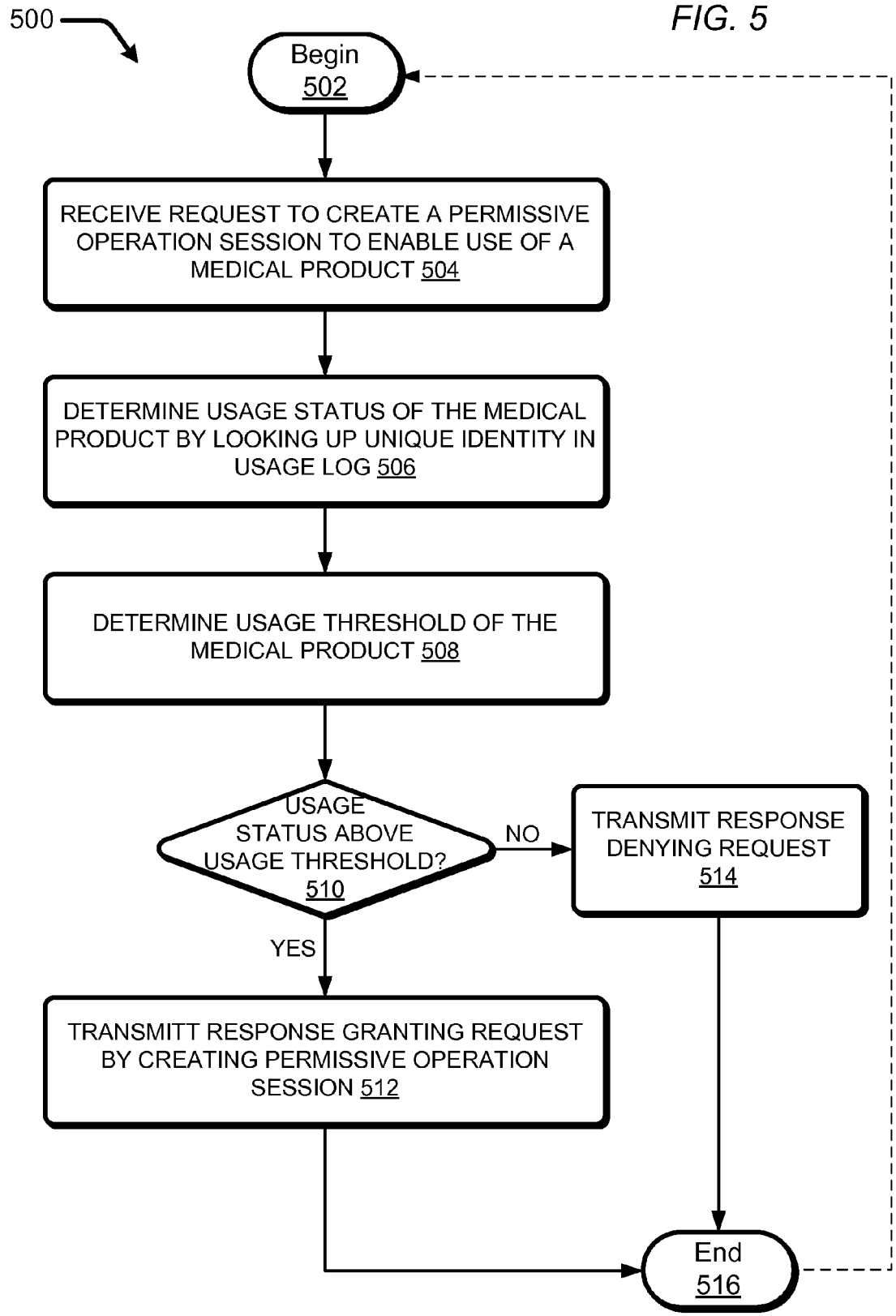
FIG. 5 is a flow chart of an exemplary process for preventing contaminated use of a medical product.

FIG. 5 is a flow diagram of an exemplary process 500 for preventing contaminated use of a medical product that becomes contaminated upon being used for an intended purpose that requires the operation of a medical treatment apparatus. The process 500 may begin at block 502, which may occur in response to an event, e.g. a user device pings an entity or system to begin performing the process 500, or may occur as a typical dormant state of an entity or system prior to commencing the process 500. At block 504, a request to create a permissive operation session to enable the use of a medical product may be received. The request may include a unique identity associated with a medical product that a medical staffer intends to use for an intended purpose. For example, a medical staffer may scan in an ID tag of the medical product with a tag reader of a medical treatment apparatus to cause a request to be sent to create a permissive operation session specifically for that particular medical product. Next, at block 506, a usage status of the medical product is determined by looking up the unique identity associated with the medical product, which was previously scanned in by the medical staffer, in a usage log. As discussed above, e.g. with reference to FIG. 4, the usage status may include an indication that the medical product is "Used," "Unused," and/or "Refurbished." These explicated usage statuses are for exemplary purposes only and are not intended to be limiting; accordingly, other usage statuses may be defined and applied.

At block 508, which may be performed before or after or contemporaneously with block 506, a usage threshold of the medical product is determined. In some implementations, medical product may be a disposable type product and, in such a case, the usage threshold may be a single permissive operation session. For example, in an implementation where the medical product is a disposable type product, such as a disposable EBC, the Usage Threshold may be indicated as "Disposable" and once the Usage Status is updated from "Unused" to "Used" the usage status cannot change to "Unused" or "Refurbished." Alternatively, in an implementation where the medical product is capable of being refurbished for reuse, such as a stainless steel surgical suction device (similar to that depicted in FIG. 3), the Usage Threshold may be indicated as "Refurbishable" and once the Usage Status is updated from "Unused" to "Used," or from "Refurbished" to "Used," the usage status may be subsequently changed to "Refurbished." Next, at decision block 510, it is determined whether the usage status is currently above the usage threshold. For example, if the usage status is equal to "Used" and the usage threshold is equal to "disposable," then it will be determined that the usage status is above the usage threshold. Alternatively, if the usage status is "Unused" and the usage threshold is either "Refurbishable" or "Disposable," then it will be determined that the usage status satisfied the usage threshold.

Following block 510, the process flow proceeds to either block 512 or block 514. In particular, if it is determined at block 510 that the usage status of the medical product does not currently exceed the usage threshold, the process flow proceeds to block 512 at which a response granting the request by creating a permissive operation session is transmitted, e.g. to an entity or system that sent the request. Alternatively, if it is determined at block 510 that the usage status of the medical product does currently exceed the usage threshold, the process flow proceeds to block 514 at which a response denying the request is transmitted, e.g. to an entity or system that sent the request, but which does not create the requested permissive operation session. In some implementations, no response is actually transmitted as it should be appreciated that an actual response transmission may not be necessary to prevent an operation of the medical treatment apparatus. However, transmitting a response may be preferential to alert a requesting entity, e.g. a medical staffer, that an alternate medical product need be selected. Following the completion of block 512 or block 514 the process flow may proceed to block 516 at which the process flow terminates and/or returns to block 502 to await another request at block 504.

It should be appreciated that although the blocks 502 through 516 are described in relation to one another, it is within the scope of the present disclosure for any particular step to be removed from the process 500 and/or reordered within process 500.

In some implementations, the process 500 may further include one or more additional or alternate operations. In particular, the process 500 may further include updating the usage status of the medical product in the usage log in response to granting the request at block 512. For example, a presumption may be made that upon a permissive operation session being created for a particular medical product, that medical product becomes contaminated through use. Accordingly, the usage status may be updated to "Used" immediately upon granting a request. Subsequently, the usage status may be again updated upon receiving an indication that the medical product has been acceptably refurbished, if the product is of a type capable of refurbishment. Furthermore, in some implementations the usage threshold may be updated. For example, a refurbishing entity may be approved to cleanse, sanitize, inspect, and/or certify various medical components and send an indication which causes the usage threshold to be changed for a particular uniquely identified medical product, or a class of medical product (e.g. identified by part number rather than an ID tag).

Figure 6:
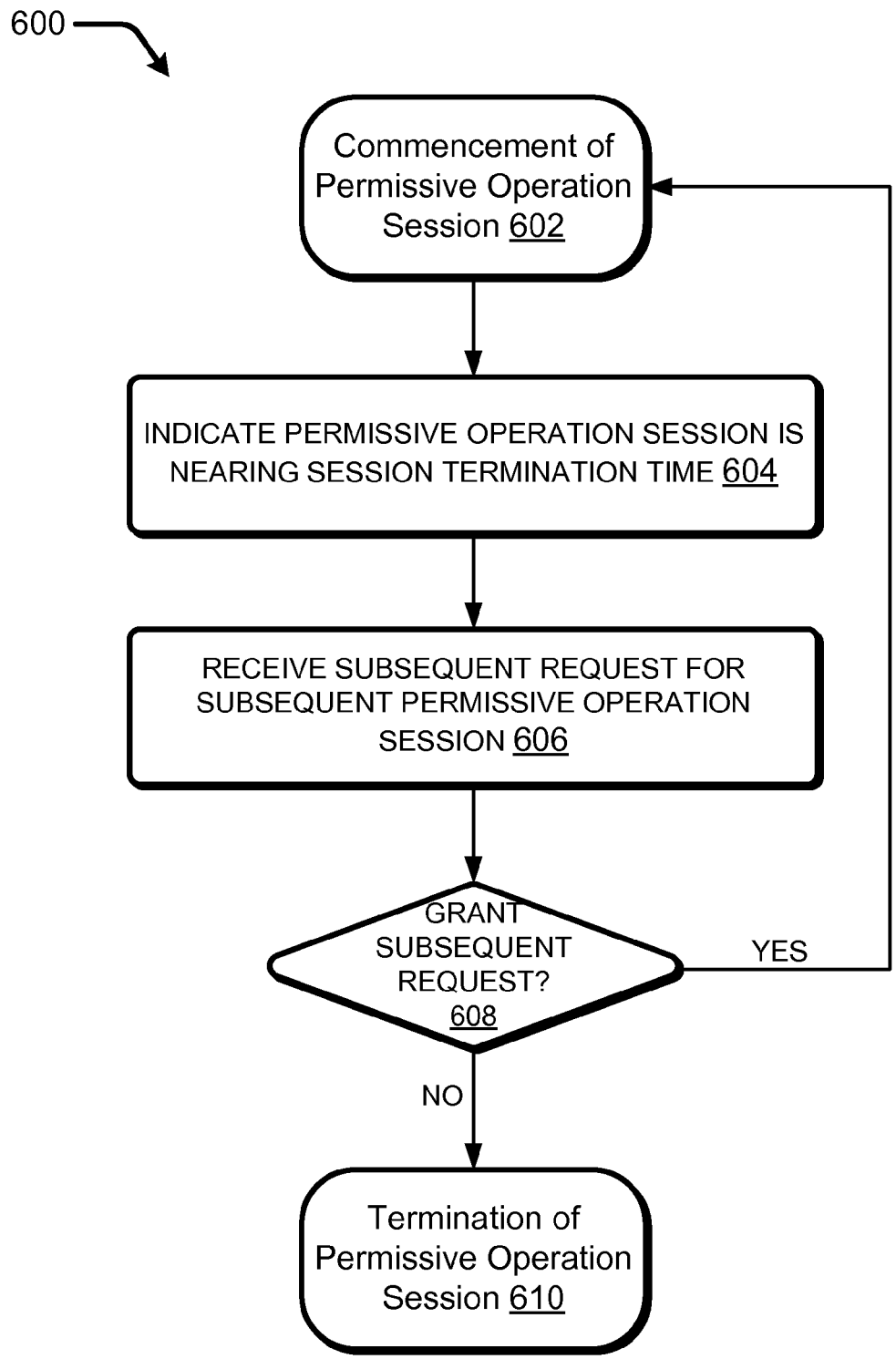
FIG. 6 is a flow chart of an exemplary process for preventing contaminated use of a medical product in a continuous use cycle.

FIG. 6 is a flow chart of an exemplary process 600 for preventing contaminated use of a medical product in a continuous use cycle. The process 600 begins at block 602 once a permissive operation session has been granted. Next, the process 600 proceeds to block 604 at which an indication may be sent to alert an entity, e.g. a medical staffer and/or a patient, that a current permissive operation session is nearing an end.

For example, as indicated in the usage log 426 (see FIG. 4), a permissive operation session may have a corresponding Session Time associated therewith. The Session Time of a particular medical product may be a "Single Use" such as an item that is disposable and must be discarded immediately after a first use. Such a medical product might include an EBC or a hypodermic needle. The Session Time of a different medical product may be a "Surgery," e.g. the length of a particular surgical operation. Such a medical product might include a surgical suction tip or a surgical forceps. Yet again, the Session Time of yet another medical product may be a particular length of time, e.g. 24 hours or 48 hours. Such a medical product might include an endotracheal suction tube (EST) for use with a 24-hour continuous-use suction system. For example, suctioning of the airways is often required in critically ill, intubated, or tracheotomised patients, and in such cases suctioning may occur continuously via an endotracheal suction tube that is left in place for 24-hours prior to requiring replacement with a non-contaminated EST so as to control unnecessary bacteria buildup. However, it may not be necessary for the same EST to remain in place for the entire 24-hour period. For example, an EST may be replaced prior to the expiration of the 24 hours thereby restarting the 24-hour continuous-use window. Accordingly, the process 600 may proceed to block 606 where a subsequent request to create a subsequent permissive operation session is received. Next, at block 608 a determination is made whether to grant or deny the request received at block 606. In some implementations, a process similar to process 500 is then performed in order to grant or deny the subsequent request. In a scenario where the subsequent request is not granted, the permissive operation session may be allowed to proceed to the termination time. For example, a 24 hour window may allowed to run out at block 610. In a scenario where the subsequent request is granted, the process 600 may proceed to back to block 602 at which the process 600 is repeated. In particular, in the event that a medical staffer replaces the EST prior to the expiration of a permissive operation session, a subsequent permissive operation session may be granted and commenced to restart a 24 hour period (or any other applicable temporal period, e.g. 18 hours or 48 hours or 15 minutes and 37 seconds).

In some implementations, the process 500 may further include terminating a permissive operation session at the expiration of a predetermined temporal period, e.g. 24 hours in accordance with the EST example above. In some implementations, the termination of the permissive operation session immediately causes the medical treatment apparatus to stop operating. For example, if a surgical procedure is determined to have been completed and the Session Time is "Surgery" then the medical treatment apparatus may be caused to stop operating. In some implementations, the termination of the permissive operation session does not immediately cause the medical treatment apparatus to stop operating. For example, an alarm may sound, indicating to a medical staffer that the permissive operation session has ended, to alert the medical staffer of a required medical product change out. To continue with the EST example introduced above, because the EST may be necessary to maintain clear airways of a patient, halting the operation of the medical treatment apparatus, e.g. a vacuum, could potentially be dangerous to the patient. Accordingly, sounding an alarm to alter medical staffers that the EST needs to be replaced with a new EST may be preferred to halting the operation of the medical treatment apparatus while the EST is actively clearing a patient's airways.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A medical device comprising:
   an extracorporeal blood circuit having an identification tag defining a unique identity associated with the extracorporeal blood circuit, the unique identity being maintained in a usage log along with other unique identities associated with other extracorporeal blood circuits;
   one or more exposure devices, directed toward an exposure region, for exposing blood circulating through the extracorporeal blood circuit to an exposure therapy during a treatment session; and
   a controller programmed to:
      prevent the one or more exposure devices from operating outside of a permissive operation session that is at least partially based on a usage status indicating whether the extracorporeal blood circuit is used or un-used,
      transmit, to a usage logger, a request for the usage status, the request including the unique identity associated with the extracorporeal blood circuit,
      receive, from the usage logger, a response that indicates the usage status, and
      based on the response indicating that the extracorporeal blood circuit is un-used, create the permissive operation session, wherein the permissive operation session expires immediately following the treatment session.

2. The medical device of claim 1, further comprising a tag reader, in communication with the controller, to identify the unique identity associated with the extracorporeal blood circuit.

3. The medical device of claim 2, further comprising a support element configured to temporarily maintain the extracorporeal blood circuit in the exposure region during the treatment session, wherein the tag reader is fixed, in location, relative to the support element, and wherein the identification tag is disposed on the extracorporeal blood circuit at a predetermined location to result in the identification tag being adjacent to the tag reader when the extracorporeal blood circuit is installed onto the support element, the identification tag being out of a range of the tag reader when the extracorporeal blood circuit is not installed onto the support element.

4. The medical device of claim 1, wherein the identification tag defining the unique identity associated with the extracorporeal blood circuit includes at least one of an electromagnetic radiation emitting tag or a visual graphic tag.

5. The medical device of claim 1, wherein the controller is further programmed to send to the usage logger a usage status update, the usage status update including the unique identity, the usage status update informing the usage logger of a first use of the extracorporeal blood circuit.

6. The medical device of claim 1, further comprising a blood pump to perfuse blood through the extracorporeal blood circuit during the treatment session, wherein the controller is further programed to prevent the blood pump from operating outside of the permissive operation session.

7. The medical device of claim 1, wherein at least a portion of the extracorporeal blood circuit is a transparent flexible tube, and wherein the support element includes a plurality of hooks configured to maintain the transparent flexible tube in a helical shape, and wherein the one or more exposure devices includes an ultraviolet light source disposed within an interior region of the helical shape.

8. The medical device of claim 7, wherein the one or more exposure devices further comprises one or more additional ultraviolet light sources disposed within an exterior region of the helical shape.

9. The medical device of claim 1, wherein the one or more exposure devices includes at least one electromechanical speaker to direct sound waves toward the exposure region during the treatment session.

10. The medical device of claim 1, wherein the one or more exposure devices includes at least one electromagnetic field (EMF) generator to controllably raise a level of magnetic flux density exposure to blood circulating through the extracorporeal blood circuit during the treatment session.

11. The medical device of claim 1, further including a housing that encloses the support element and the one or more exposure devices, the one or more exposure devices including at least one ultraviolet light source, wherein the housing includes an internal surface at least a portion of which is reflective to redirect ultraviolet light toward the extracorporeal blood circuit.

12. A method executed on one or more computers for preventing a contaminated use of one or more medical products that become contaminated upon being used for an intended purpose, the intended purpose requiring operation of a medical treatment apparatus, the method comprising the steps of:
   receiving a request to create a permissive operation session of the medical treatment apparatus to enable use of a first medical product for the intended purpose, the request including a first unique identity associated with the first medical product;
   determining a usage status of the first medical product by looking up the first unique identity in a usage log, the usage status being associated with the first unique identity;
   transmitting a response to the request based at least in part on the usage status, the response granting the request by creating the permissive operation session in response to one or more processors determining that the usage status satisfies a usage threshold; and
   prior to a session termination time of the permissive operation session, granting a subsequent request to create a subsequent permissive operation session of the medical treatment apparatus to enable use of a second medical product for the intended purpose, the subsequent request including a second unique identity associated with the second medical product.

13. The method of claim 12, wherein the first medical product is a disposable medical product and the usage threshold is a single permissive operation session such that the transmitting the response includes granting the request by creating the permissive operation session in response to determining that the usage status indicates that the disposable medical product has never been previously used in a past permissive operation session.

14. The method of claim 12, further comprising updating the usage status of the first medical product in the usage log in response to the granting the request by creating the permissive operation session.

15. The method of claim 12, further comprising:
   receiving an indication that the first medical product was refurbished following a past permissive operation session; and
   updating at least one of the usage status or the usage threshold, or both, of the first medical product based on the indication.

16. The method of claim 12, wherein the permissive operation session extends for a predetermined period of time circumscribed by a session commencement time and the session termination time, the operation of the medical treatment apparatus being unrestricted after the session commencement time until being restricted at the session termination time.

17. The method of claim 12, wherein the first unique identity associated with the first medical product is embodied in an identification tag that is integrated into the first medical product and the identification tag is readable by an electronic tag reader.

18. The method of claim 12, further comprising:
   prior to the session termination time of the permissive operation session, indicating that the permissive operation session is nearing the session termination time.

* * * * *